(12) United States Patent
Cao et al.

(10) Patent No.: US 7,378,095 B2
(45) Date of Patent: *May 27, 2008

(54) METHODS OF TREATING TYPE I DIABETES BY BLOCKING VEGF-MEDIATED ACTIVITY

(75) Inventors: Jingtai Cao, Chappaqua, NY (US); Li-Hsien Wang, Somers, NY (US); Hsin Chieh Lin, Yorktown Heights, NY (US); Mark W. Sleeman, Mahopac, NY (US); Stanley J. Wiegand, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 300 days.

This patent is subject to a terminal disclaimer.

(21) Appl. No.: 11/193,746

(22) Filed: Jul. 29, 2005

(65) Prior Publication Data

US 2006/0024309 A1 Feb. 2, 2006

Related U.S. Application Data

(60) Provisional application No. 60/592,628, filed on Jul. 30, 2004.

(51) Int. Cl.
*A61K 38/18* (2006.01)
*C07K 14/71* (2006.01)
*C12N 15/62* (2006.01)

(52) U.S. Cl. .............................. 424/134.1; 424/192.1; 514/2; 514/12; 530/350; 536/23.4

(58) Field of Classification Search .................. None
See application file for complete search history.

(56) References Cited

U.S. PATENT DOCUMENTS

| 6,524,583 | B1 * | 2/2003 | Thorpe et al. ........... 424/145.1 |
| 6,833,349 | B2 | 12/2004 | Xia et al. |
| 2003/0044841 | A1 | 3/2003 | Baker et al. |
| 2005/0260203 | A1 * | 11/2005 | Wiegand et al. ......... 424/145.1 |
| 2006/0030529 | A1 * | 2/2006 | Wiegand et al. .............. 514/12 |

FOREIGN PATENT DOCUMENTS

| WO | WO 00/75319 | 12/2000 |
| WO | WO 02/060489 | 8/2002 |
| WO | WO 2004/087206 | 10/2004 |

OTHER PUBLICATIONS

Flyvbjerg, A., et al, (2002) Diabetes 5:3090-3094.
Eremina, E., et al., (2003) J. Clin. Invest. 111:707-716.
De Vriese, A., et al., (2001) J. Am. Soc. Nephrol. 12:993-1000.
Kobayashi, T., et al, (2002) Am. J. Physiol. Heart Circ. Physiol. 283(5): H1761-H1768.
Chiarelli, F., et al., (2000) Diabetic Medicine 17(9):650-656.

* cited by examiner

*Primary Examiner*—Christine J Saoud
*Assistant Examiner*—Jon M Lockard
(74) *Attorney, Agent, or Firm*—Valeta Gregg, Esq.

(57) ABSTRACT

Methods of treating diabetes in mammals, particularly humans, by blocking or inhibiting VEGF-mediated activity. A preferred inhibitor of VEGF-mediated activity is a VEGF antagonist such as the VEGF fusion protein trap of SEQ ID NO:2 capable of binding and blocking VEGF. The method of the invention may be combined with other therapies, such as with insulin therapy.

5 Claims, 2 Drawing Sheets

SEQUENCE LISTING

<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtgggggatt     480 gacttcaact gggaatacccc ttcttcgaag catcagcata gaaaacttgt aaaccgagac     540
ctaaaaaccc agtctgggag tgagatgaag aaattttttga gcaccttaac tatagatggt     600
gtaacccgga gtgaccaagg attgtacacc tgtgcagcat ccagtgggct gatgaccaag     660
```

-continued

```
aagaacagca catttgtcag ggtccatgaa aaggacaaaa ctcacacatg cccaccgtgc      720
ccagcacctg aactcctggg gggaccgtca gtcttcctct tccccccaaa acccaaggac      780
accctcatga tctcccggac ccctgaggtc acatgcgtgg tggtggacgt gagccacgaa      840
gaccctgagg tcaagttcaa ctggtacgtg gacggcgtgg aggtgcataa tgccaagaca      900
aagccgcggg aggagcagta caacagcacg taccgtgtgg tcagcgtcct caccgtcctg      960
caccaggact ggctgaatgg caaggagtac aagtgcaagg tctccaacaa agccctccca     1020
gcccccatcg agaaaaccat ctccaaagcc aagggcagc cccgagaacc acaggtgtac      1080
accctgcccc catcccggga tgagctgacc aagaaccagg tcagcctgac ctgcctggtc     1140
aaaggcttct atcccagcga catcgccgtg gagtgggaga gcaatgggca gccggagaac     1200
aactacaaga ccacgcctcc cgtgctggac tccgacggct ccttcttcct ctacagcaag     1260
ctcaccgtgg acaagagcag gtggcagcag gggaacgtct tctcatgctc cgtgatgcat     1320
gaggctctgc acaaccacta cacgcagaag agcctctccc tgtctccggg taaatga        1377
```

<210> SEQ ID NO 2
<211> LENGTH: 458
<212> TYPE: PRT
<213> ORGANISM: homo sapiens

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
```

-continued

```
                    245                 250                 255
Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
            450                 455
```

METHODS OF TREATING TYPE I DIABETES BY BLOCKING VEGF-MEDIATED ACTIVITY

RELATED APPLICATIONS

This application claims the benefit under 35 U.S.C. 119(e) to U.S. Ser. No. 60/592,628 filed 30 Jul. 2004, which application is incorporated by reference in its entirety.

BACKGROUND

1. Field of the Invention

The field of the invention is generally related to methods of treating diabetes by administering agents capable of decreasing serum glucose levels. In particular, the field of the invention is methods of treating type I diabetes by administering agents capable of blocking, inhibiting, or ameliorating VEGF-mediated activity.

2. Description of Related Art

Streptozotocin (STZ)-induced diabetes is widely accepted as an animal model for human type I diabetes (see, for example, Susztak et al. (2004) Diabetes 53:784-794).

Vascular endothelial growth factor (VEGF) has been recognized as a primary stimulus of angiogenesis in pathological conditions. Approaches to methods of blocking VEGF are described, for example, in PCT WO/0075319 which describes a VEGF-specific fusion protein which binds and inhibits VEGF.

BRIEF SUMMARY OF THE INVENTION

The present invention is based, in part, on the observation that administration of a vascular endothelial growth factor (VEGF) antagonist is able to return blood glucose levels to normal in an animal model of human type I diabetes.

Accordingly, in a first aspect, the invention features a method of treating type I diabetes in a subject, comprising administering to the subject an agent capable of blocking, inhibiting, or ameliorating VEGF-mediated activity. In specific embodiments, the method of treatment of the invention results in decreased serum glucose levels, improved glucose tolerance, and/or improved glycemic control.

The agent capable of blocking, inhibiting, or ameliorating VEGF-mediated activity in specific embodiments is a VEGF antagonist. More specifically, the VEGF antagonist is a VEGF trap antagonist is a fusion protein selected from the group consisting of acetylated Flt-1(1-3)-Fc, Flt-1(1-3$_{R\rightarrow N}$) Flt-1(1-3$_{\Delta B}$)-Fc, Flt-1(2-3$_{\Delta B}$)-Fc, Flt-1(2-3)-Fc, Flt-1D2-VEGFR3D3-Fc$\Delta$C1(a), Flt-1D2-Flk-1D3-Fc$\Delta$C1(a), and VEGFR1R2-Fc$\Delta$C1(a) (SEQ ID NOs:1-2). In a preferred embodiment, the VEGF antagonist is VEGFR1R2-Fc$\Delta$C1(a). In other embodiments, the VEGF antagonist is a VEGF-specific antibody, a nucleic acid such as an inhibitory ri0bozyme or antisense molecule, a small molecule, an aptamer, a carbohydrate, peptidomimetic, or hapten.

Administration of the agent may be by any method known in the art, including subcutaneous, intramuscular, intradermal, intraperitoneal, intravenous, intranasal, or oral routes of administration. Preferred methods of administered a VEGF trap antagonist is by subcutaneous or intravenous administration.

The subject treated is preferably a human suffering from type I diabetes.

Other objects and advantages will become apparent from a review of the ensuing detailed description.

DETAILED DESCRIPTION

Figure 1:
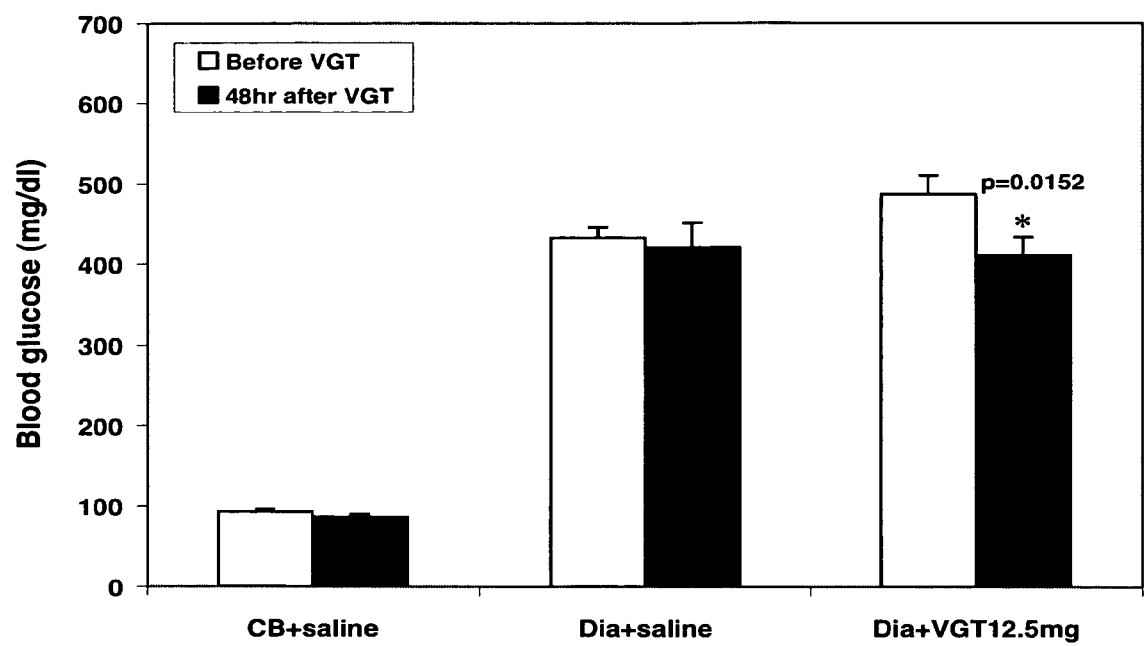
FIG. 1. A single injection of VEGF trap antagonist significantly reduces blood glucose levels in diabetic rats. Normal control rats (CB+saline, n=4); Diabetic rats treated with saline (STZ+saline, n=6); Diabetic rats treated with VEGF trap (VGT) (12.5 mg/kg) (Dia+VGT 12.5 mg, n=6).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General Description

The invention is based in part on the finding that administration of an agent capable of blocking or inhibiting VEGF-mediated activity is capable of decreasing serum glucose and improving glucose disposal in an animal model of human type I diabetes. These findings represent the first time an agent capable of blocking or inhibiting VEGF-mediated activity has been shown to ameliorate type I diabetes. Thus, the invention provides for methods of treating diabetes in a mammal by administering a VEGF antagonist. More specifically, the method of the invention may be practiced with a VEGF antagonist such as a dimeric protein composed of two fusion polypeptides ("VEGF trap") (SEQ ID NO:2), as shown below, or a VEGF-specific antibody.

Definitions

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of a VEGF blocker or inhibitor is a VEGF receptor-based antagonist including, for example, an anti-VEGF antibody, or a VEGF trap such as VEGFR1R2-FcΔC1(a) (SEQ ID NOs:1-2). For a complete description of VEGF-receptor based antagonists including VEGFR1R2-FcΔC1(a), see PCT publication WO/00/75319, the contents of which is incorporated in its entirety herein by reference.

A "small molecule" is defined herein to have a molecular weight below about 500 Daltons, and may include chemical as well as peptide molecules.

Nucleic Acid Constructs

Individual components of the VEGF-specific fusion proteins of the invention may be constructed by molecular biological methods known to the art with the instructions provided by the instant specification. These components are selected from a first cellular receptor protein, such as, for example, VEGFR1; a second cellular receptor protein, such as, for example, VEGFR2; a multimerizing component, such as an Fc.

Specific embodiments of the VEGF-specific fusion proteins useful in the methods of the invention comprise a multimerizing component which allows the fusion proteins to associate, e.g., as multimers, preferably dimers. Preferably, the multimerizing component comprises an immunoglobulin derived domain. Suitable multimerizing components are sequences encoding an immunoglobulin heavy chain hinge region (Takahashi et al. 1982 Cell 29:671-679); immunoglobulin gene sequences, and portions thereof.

The nucleic acid constructs encoding the fusion proteins useful in the methods of the invention are inserted into an expression vector by methods known to the art, wherein the nucleic acid molecule is operatively linked to an expression control sequence. Host-vector systems for the production of proteins comprising an expression vector introduced into a host cell suitable for expression of the protein are known in the art. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

Antisense Nucleic Acids

In one aspect of the invention, VEGF-mediated activity is blocked or inhibited by the use of VEGF antisense nucleic acids. The present invention provides the therapeutic or prophylactic use of nucleic acids comprising at least six nucleotides that are antisense to a gene or cDNA encoding VEGF or a portion thereof. As used herein, a VEGF "antisense" nucleic acid refers to a nucleic acid capable of hybridizing by virtue of some sequence complementarity to a portion of an RNA (preferably mRNA) encoding VEGF. The antisense nucleic acid may be complementary to a coding and/or noncoding region of an mRNA encoding VEGF. Such antisense nucleic acids have utility as compounds that prevent VEGF expression, and can be used in the treatment of diabetes. The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The VEGF antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. In addition, the antisense molecules may be polymers that are nucleic acid mimics, such as PNA, morpholino oligos, and LNA. Other types of antisence molecules include short double-stranded RNAs, known as siRNAs, and short hairpin RNAs, and long dsRNA (>50 bp but usually ≧500 bp).

Inhibitory Ribozymes

In another aspect of the invention, diabetes may be treated in a subject suffering from such disease by decreasing the level of VEGF activity by using ribozyme molecules designed to catalytically cleave gene mRNA transcripts encoding VEGF, preventing translation of target gene mRNA and, therefore, expression of the gene product.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246. While ribozymes that cleave mRNA at site-specific recognition sequences can be used to destroy mRNAs encoding VEGF, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art. The ribozymes of the present invention also include RNA endoribonucleases (hereinafter "Cech-type ribozymes") such as the one that occurs naturally in *Tetrahymena thermophila* (known as the IVS, or L-19 IVS RNA). The Cech-type ribozymes have an eight base pair active site that hybridizes to a target RNA sequence where the cleavage of the target RNA takes place. The invention encompasses those Cech-type ribozymes that target eight base-pair active site sequences that are present in the gene encoding VEGF.

Generation of Antibodies to VEGF Proteins

In another aspect of the invention, the invention may be practiced with an anti-VEGF antibody or antibody fragment capable of binding and blocking VEGF activity. Anti-VEGF antibodies are disclosed, for example, in U.S. Pat. No. 6,121,230, herein specifically incorporated by reference. The term "antibody" as used herein refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (eg. $IgG_1$, $IgG_2$, etc.). Typically, the antigen-binding region of an antibody will be the most critical in determining specificity and affinity of binding.

Antibodies exist as intact immunoglobulins, or as a number of well-characterized fragments produced by digestion with various peptidases. For example, pepsin digests an antibody below the disulfide linkages in the hinge region to produce F(ab)'$_2$, a dimer of Fab which itself is a light chain joined to V$_H$-C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms antibody, as used herein, also includes antibody fragments either produced by the modification of whole antibodies, or those synthesized de novo using recombinant DNA methodologies (e.g., single chain Fv) (scFv) or those identified using phage display libraries (see, for example, McCafferty et al. (1990) Nature 348:552-554).

Methods for preparing antibodies are known to the art. See, for example, Kohler & Milstein (1975) Nature 256: 495-497; Harlow & Lane (1988) *Antibodies: a Laboratory Manual*, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma and plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the fusion proteins and methods of the instant invention. Also, transgenic mice, or other organisms such as other mammals, may be used to express human or humanized antibodies. Alternatively, phage display technology can be used to identify antibodies and heteromeric Fab fragments that specifically bind to selected antigens.

Antibody Screening and Selection. Screening and selection of preferred antibodies can be conducted by a variety of methods known to the art. Initial screening for the presence of monoclonal antibodies specific to a target antigen may be conducted through the use of ELISA-based methods, for example. A secondary screen is preferably conducted to identify and select a desired monoclonal antibody for use in construction of the multi-specific fusion proteins of the invention. Secondary screening may be conducted with any suitable method known to the art. One preferred method, termed "Biosensor Modification-Assisted Profiling" ("BiaMAP") is described in co-pending U.S. Ser. No. 10/699, 361 filed 31 Oct. 2003, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody:antigen interactions.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Cellular Transfection and Gene Therapy

The present invention encompasses the use of nucleic acids encoding the VEGF-specific fusion proteins of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. Reintroduction of transfected cells may be accomplished by any method known to the art, including re-implantation of encapsulated cells. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of treating diabetes in a human comprising transfecting a cell with a nucleic acid encoding a VEGF-specific fusion protein of the invention, wherein the nucleic acid comprises an inducible promoter operably linked to the nucleic acid encoding the VEGF-specific fusion protein. For gene therapy procedures in the treatment or prevention of human disease, see for example, Van Brunt (1998) Biotechnology 6:1149-1154.

Combination Therapies

In some embodiments, the VEGF-specific fusion proteins of the present invention may be administered in combination with insulin or an insulin derivative. Combination therapy includes administration of a single pharmaceutical dosage formulation which contains a VEGF-specific fusion protein and insulin; as well as administration of a VEGF-specific fusion protein pharmaceutical dosage formulation and insulin in its own separate pharmaceutical dosage formulation. For example, a VEGF-specific fusion protein of the invention and insulin can be administered to the patient together in a single oral dosage composition such as a tablet or capsule, or each agent administered in separate oral dosage formulations. Where separate dosage formulations are used, the VEGF-specific fusion protein of the invention and insulin can be administered at essentially the same time, i.e., concurrently, or at separately staggered times, i.e., sequentially. In specific embodiments, insulin may be delivered through islet cell transfer or using infusion pump.

Pharmaceutical Compositions

Pharmaceutical compositions useful in the practice of the method of the invention include a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous, subcutaneous, or intramuscular administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention that will be effective in the treatment of diabetes can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

The invention also provides an article of manufacturing comprising packaging material and a pharmaceutical agent contained within the packaging material, wherein the pharmaceutical agent comprises at least one VEGF-specific fusion protein of the invention and wherein the packaging material comprises a label or package insert which indicates that the VEGF-specific fusion protein can be used for treating diabetes.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

A single injection of VEGF Trap reduces blood glucose levels in a rat model of Type I diabetes.

Adult, male Sprague Dawley rats (n=16) were fasted overnight and diabetes was induced in 12 rats by administration of a single, intraperitoneal injection of streptozotocin (60-mg/kg, in 10 mM citrate buffer, pH 4.5). Four animals were injected with citrate buffer (CB) alone and served as non-diabetic controls. Within 24 hours of streptozotocin (STZ) treatment, the average blood glucose level in rats received STZ injections was increased to 367.8±30.7 mg/dL, compared to 103.0±4.55 mg/dL in the control rats. Insulin levels were undetectable in STZ-injected rats, confirming the induction of diabetes. Blood glucose levels were monitored weekly to ensure that diabetic status was maintained in rats received STZ-injection. Two week after the STZ injection, 12 STZ-injected rats were divided into two groups. One group (n=6) received VEGF trap (12.5 mg/kg) (SEQ ID NO:2) injection subcutaneously. The other group (n=6), as well as the control rats group (n=4) received equivalent volume of saline solution injection subcutaneously. The blood glucose levels in all rats were measured right before the VEGF trap or saline injections and 48 hours later the injections. The ANOVA and paired t-test were used in statistic analysis.

As shown in FIG. 1, the blood glucose levels in VEGF trap treated STZ-induced diabetic rats were significantly lower than the blood glucose levels before the VEGF trap treatment. In contrast, there were no significant changes in the blood glucose levels in STZ-induced diabetic rats received saline injections. As expected, there were also no changes in the blood glucose levels in control rats received injections.

Example 2

Chronic administration of VEGF Trap to diabetic mice results in a progressive reduction in blood glucose to normal glycemic levels.

Figure 2:
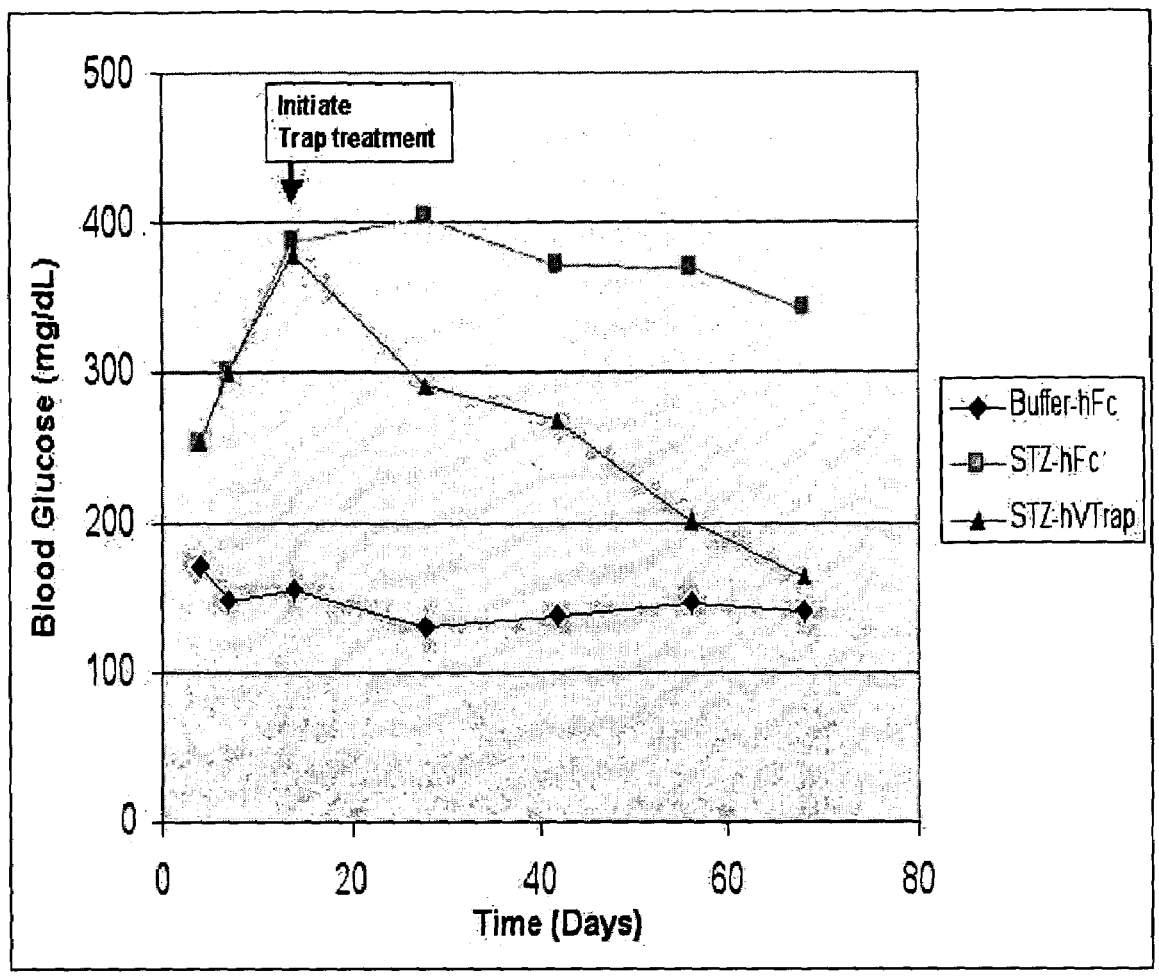
FIG. 2. Changes in blood glucose levels produced by repeated administration of VEGF trap in diabetic mice. Normal control mice (CB) treated with a control protein (hFc, n=7, —♦—); Diabetic mice (STZ-induced) treated with VEGF trap (hVTrap, n=9, —▲—); Diabetic mice (STZ-induced) treated with a control protein (hFc, n=9, —■—).

Apolipoprotein E (APOE) deficient mice were rendered diabetic by 5 consecutive daily intraperitoneal injections of streptozotocin (STZ) at the dose of (60 mg/kg, in citrate buffer). Control mice were received citrate buffer (CB) only. The blood glucose levels were measured 4 days after the final injections of STZ or CB and were monitored daily thereafter. While the blood glucose levels maintained relatively unchanged in the control ice, the blood glucose levels in mice received STZ injections elevated gradually and more than doubled after 14 days following the STZ injections (FIG. 2). STZ-induced diabetic mice were then divided into two groups. One group received subcutaneous injections of VEGF trap (12.5 mg/kg) (SEQ ID NO:2) while the other group and the control mice received subcutaneous injections of a control protein (hFc, comprising the Fc domain of human IgG) twice per week for eight weeks. The blood glucose levels were measured every two weeks. Two weeks after the initiation of the VEGF trap treatment, the blood glucose levels in those STZ-induced diabetic mice received the VEGF trap were already significant lower than the blood glucose levels in those mice received the control protein. While the blood glucose levels remained elevated in control STZ-induced diabetic mice, the blood glucose levels continued to decrease gradually in STZ-induced diabetic mice received VEGF trap treatment. After 8 weeks, the blood glucose levels in STZ-induced diabetic mice received VEGF trap treatment decreased almost to the levels in those non-diabetic control mice (FIG. 2).

The present invention may be embodied in other specific forms without departing from the spirit or essential attributes thereof.

We claim:

1. A method of treating type I diabetes in a subject, comprising administering to the subject an agent which inhibits vascular endothelial growth factor (VEGF) activity such that diabetes is treated, wherein the agent is VEGFR1R2-FcΔC1 (a) (SEQ ID NO:2).

2. The method of claim 1 wherein the treatment of diabetes results in one or more of decreased serum glucose concentrations, improved glucose tolerance, and improved glycemic control.

3. The method of claim 1, wherein administration is via subcutaneous, intramuscular, intradermal, or intravenous routes.

4. The method of claim 1, wherein the agent is administered with a second compound.

5. The method of claim 4, wherein the second compound is insulin.

* * * * *